United States Patent [19]

Bolich, Jr. et al.

[11] Patent Number: 5,662,892
[45] Date of Patent: Sep. 2, 1997

[54] PERSONAL CARE COMPOSITIONS CONTAINING HYDROPHOBIC LINEAR COPOLYMER AND HYDROPHOBIC, VOLATILE, BRANCHED HYDROCARBON SOLVENT

[75] Inventors: Raymond Edward Bolich, Jr., Maineville; Sanjeev Midha, Blue Ash, both of Ohio

[73] Assignee: The Procter & Gamble Company, Cincinnati, Ohio

[21] Appl. No.: 616,402

[22] Filed: Mar. 15, 1996

[51] Int. Cl.⁶ .............................. A61K 7/06; A61K 7/075
[52] U.S. Cl. ............... 424/70.1; 424/70.11; 424/70.16; 424/70.19; 424/70.21; 424/70.23; 424/70.27; 424/70.24; 424/70.28; 424/70.31
[58] Field of Search ................. 424/70.1, 70.11, 424/70.23, 70.16, 70.19, 70.28, 70.24, 70.31, 70.27, 70.21

[56] References Cited

U.S. PATENT DOCUMENTS

| | | | |
|---|---|---|---|
| 3,697,643 | 10/1972 | Sheperd et al. | 424/63 |
| 3,907,984 | 9/1975 | Calvert et al. | 424/47 |
| 4,059,688 | 11/1977 | Rosenberg et al. | 424/71 |
| 4,722,958 | 2/1988 | Sauer et al. | 524/379 |
| 4,798,721 | 1/1989 | Yahagi et al. | 424/70 |
| 4,963,348 | 10/1990 | Bolich, Jr. et al. | 424/71 |
| 4,981,902 | 1/1991 | Mitra et al. | 524/547 |
| 4,981,903 | 1/1991 | Garbe et al. | 524/547 |
| 4,985,239 | 1/1991 | Yahagi et al. | 424/70 |
| 4,988,506 | 1/1991 | Mitra et al. | 424/81 |
| 5,009,880 | 4/1991 | Grollier et al. | 424/47 |
| 5,019,377 | 5/1991 | Torgerson | 424/70 |
| 5,021,477 | 6/1991 | Garbe et al. | 424/70 |
| 5,073,371 | 12/1991 | Turner et al. | 424/401 |
| 5,073,372 | 12/1991 | Turner et al. | 424/401 |
| 5,104,642 | 4/1992 | Wells et al. | 424/47 |
| 5,120,531 | 6/1992 | Wells et al. | 424/70 |
| 5,120,532 | 6/1992 | Wells et al. | 424/70 |
| 5,166,276 | 11/1992 | Hayama et al. | 525/329 |
| 5,219,560 | 6/1993 | Suzuki et al. | 424/63 |
| 5,223,179 | 6/1993 | Connor et al. | 252/548 |
| 5,256,407 | 10/1993 | Gough | 424/71 |
| 5,286,755 | 2/1994 | Kauffmann et al. | 514/944 |
| 5,290,555 | 3/1994 | Guthauser et al. | 424/401 |
| 5,324,507 | 6/1994 | Dubief et al. | 424/70 |
| 5,356,627 | 10/1994 | Da Cunha et al. | 424/401 |
| 5,362,485 | 11/1994 | Hayama et al. | 424/70 |
| 5,372,804 | 12/1994 | Khoshdel et al. | 424/59 |
| 5,374,421 | 12/1994 | Tashiro et al. | 424/70.12 |
| 5,391,368 | 2/1995 | Gerstein | 424/70.13 |

FOREIGN PATENT DOCUMENTS

| | | | |
|---|---|---|---|
| 647849 | 6/1992 | Australia . | |
| 0 412704 A2 | 2/1991 | European Pat. Off. | A61K 7/06 |
| 4314305 A1 | 3/1994 | Germany | A61K 7/11 |
| 2-25411 | 1/1990 | Japan . | |
| WO 92/21319 | 12/1992 | WIPO | A61K 7/06 |
| WO 95/04518 | 2/1995 | WIPO | A61K 7/06 |
| WO 95/05800 | 3/1995 | WIPO | A61K 7/48 |

OTHER PUBLICATIONS

U.S. Ser. No. 08/445,267 docket No. 5329C Torgerson et al. filing date May 19, 1995.
U.S. Ser. No. 08/370,147 docket No. 5535 Midha et al. filing date Jan. 9, 1995.
U.S. Ser. No. 08/426,322 docket No. 5652 Torge et al. filing date Apr. 21, 1995.
U.S. Ser. No. 08/616,847 docket No. 5993 Midha et al. filing date Mar. 15, 1996.
U.S. Ser. No. 08/616,401 docket No. 5995 Schraer et al. filing date Mar. 15, 1996.

*Primary Examiner*—Thurman K. Page
*Assistant Examiner*—Sharon Howard
*Attorney, Agent, or Firm*—Loretta J. Henderson; Anthony D. Sabatelli

[57] ABSTRACT

The present invention relates to personal care compositions, especially hair care compositions, containing hydrophobic, linear random copolymers and a hydrophobic, volatile, branched hydrocarbon solvent for the copolymer. The copolymer is formed by the copolymerization of monomer units that form a homopolymer having a $T_g$ of at least 90° C., and monomer units that form a homopolymer having a $T_g$ of less than 25° C. The hydrocarbon solvent consists essentially of one or more branched chain hydrocarbons containing from 10 to 16 carbon atoms. The invention relates to hair styling and conditioning products such as rinses, leave on conditioners, and combination shampoo products useful for cleansing, styling and conditioning the hair.

21 Claims, No Drawings

PERSONAL CARE COMPOSITIONS CONTAINING HYDROPHOBIC LINEAR COPOLYMER AND HYDROPHOBIC, VOLATILE, BRANCHED HYDROCARBON SOLVENT

TECHNICAL FIELD

The present invention relates to personal care compositions, especially hair care compositions, containing a hydrophobic linear copolymer and a hydrophobic, volatile, branched hydrocarbon solvent for the copolymer. Examples of hair care compositions to which this invention relates are hair conditioners and hair styling agents including rinses, leave on conditioners, and combination shampoo products useful for cleansing, styling and conditioning the hair.

BACKGROUND OF THE INVENTION

The use of polymeric materials in hair care products is of increasing importance. In the hair care area, polymers can be used for hair hold and setting products, for hair conditioning products, and in shampoos. For example, rinse-off hair care conditioning/styling products typically comprise a hydrophobic polymer which remains after rinsing the hair. The polymer is solubilized in a suitable solvent which evaporates to leave the polymer treated hair. The solvent must be one in which the polymer is substantially soluble (i.e., the solvent is generally hydrophobic).

A hair styling polymer should provide certain styling benefits. For example, the styling polymer should not leave the hair feeling and looking coated. Also, the styling polymer should have sufficient adhesion without being unduly brittle such that the hair can be restyled, e.g., with heated implements, and then maintain the new style. Still in addition, the styling polymer should be deliverable from a shampoo matrix, i.e., they should deposit on the hair during the washing process and remain behind on the hair fibers. Therefore, in the hair styling area, it is desirable to provide polymers which provide improved styling benefits and which can be delivered from a wide variety of matrices, including rinses, leave-on compositions, and shampoos. It is also desirable to provide hair styling compositions which have improved hair feel performance (after application and drying of such compositions) at a particular level of hair styling or conversely, improved hair styling for a particular level of hair feel performance.

Hair styling compositions have included copolymers of hydrophobic monomers. See, e.g., EPA 92913354.4, published May 23, 1994. While such compositions provide certain hair care benefits, there remains the need for alternative hair care polymers having improved hair styling benefits and adhesive properties.

The formulation of an improved hair styling composition presents particular challenges. Not only must the polymer be capable of providing the desired styling benefits including adhesive properties, it must be formulated such that these properties are readily delivered to the hair. Thus the polymer must be suitably solubilized in the composition.

The linear copolymers of the present invention are hydrophobic materials derived from certain monomers which provide certain solubility and thermomechanical properties, more particularly desired properties of defined solvent solubility, low water solubility, and high Tg. These characteristics make these copolymers highly useful for formulation in hair care products. For example, the polymers of the present invention tend to have improved hair styling benefits (low tendency to clump, make hair look dirty or impart hair stickiness) and good adhesive properties without unacceptable brittleness such that the hair styling benefits are maintained.

It is an object of the present invention to provide hair care compositions containing certain hydrophobic linear copolymers.

It is another object of the present invention to provide hair care compositions having improved style and hold benefits.

It is another object of the present invention to provide novel hair care compositions having improved conditioning benefits.

It is a further object to provide hair care compositions that provide good hair styling benefits (e.g., having a low tendency to clump, make hair look dirty or impart hair stickiness, and good adhesive properties without unacceptable brittleness such that the hair styling benefits are maintained).

These and other objects will become readily apparent from the detailed description which follows.

SUMMARY OF THE INVENTION

The present invention relates to personal care compositions, preferably hair care compositions, comprising:

a) a hydrophobic linear random copolymer formed from the copolymerization of A monomer units and B monomer units, said A monomer units being copolymerizable with said B monomer units and selected from monomer units that form a homopolymer having a $T_g$ of at least about 90° C., said B monomer units being copolymerizable with said A monomer units and selected from monomer units that form a homopolymer having a $T_g$ of less than about 25° C.; wherein said copolymer comprises:
  (i) from about 5% to about 90% by weight of said A monomer units, and
  (ii) from about 10% to about 95% by weight of said B monomer units; said copolymer comprising randomly repeating units of said A monomer units copolymerized with said B monomer units, said copolymer having a weight average molecular weight greater than about 10,000 and a Tg of at least about 30° C., preferably about 35° to about 75° C., more preferably about 35° to about 60° C.; and (b) a hydrophobic, volatile, branched hydrocarbon solvent for said copolymer, said solvent consisting essentially of one or more branched chain hydrocarbons containing from about 10 to 16 carbon atoms; wherein the weight ratio of said copolymer to said solvent is from about 0.1% to about 50%.

In further embodiments, the present invention relates to methods for styling and/or holding hair.

In further embodiments, the present invention relates to methods for conditioning the hair.

All percentages and ratios used herein are by weight of the total composition and all measurements made are at 25° C., unless otherwise designated. The invention hereof can comprise, consist of, or consist essentially of, the essential as well as optional ingredients and components described herein. All documents referred to herein, including all patents, patent applications, and printed publications, are hereby incorporated by reference in their entirety in this disclosure.

DETAILED DESCRIPTION OF THE INVENTION

Hair Styling Polymer

The hair care compositions of the present invention comprise a hydrophobic, hair styling polymer which is a hydrophobic, random, linear copolymer (alternatively referred to herein as "linear copolymer(s)"). In general the hair care compositions comprise from about 0.1% to about 25%, preferably from about 0.5% to about 20%, and more preferably from about 0.5% to about 10%, and most preferably from about 1% to about 5% of the copolymer, although higher or lower amounts can be used depending upon the application.

The linear copolymers hereof consist essentially of monomer units which are polymerizable hydrophobic monomers. The term "hydrophobic" is used herein consistent with its standard meaning of lacking affinity for water; whereas "hydrophilic" is used herein consistent with its standard meaning of having affinity for water. As used herein in relation to monomer units or polymeric materials, "hydrophobic" means substantially water insoluble; "hydrophilic" means substantially water soluble.

As used herein in reference to the copolymer and the solvent for the copolymer, "substantially water insoluble" shall refer to a material that is not soluble in distilled (or equivalent) water, at 25° C., at a concentration of 0.2% by weight, and preferably not soluble at 0.1% by weight (calculated on a water plus monomer or polymer weight basis). As used herein in reference to the copolymer and the solvent for the copolymer, "substantially water soluble" shall refer to a material that is soluble in distilled (or equivalent) water, at 25° C., at a concentration of 0.2% by weight, and are preferably soluble at 1.0% by weight. The weight average molecular weight for purposes of determining substantial water solubility or insolubility of a polymeric material shall be about 10,000, although solubility at higher molecular weight shall also be indicative of solubility at about 10,000. "Soluble", "solubility" and the like for purposes hereof corresponds to the maximum concentration of monomer or polymer, as applicable, that can dissolve in water of other solvent to form a solution that is substantially clear to the naked eye, as is well understood to those skilled in the art. The aforementioned definitions shall also apply to other materials so described herein, to the extent any other definitions regarding such materials are consistent with those stated above.

The linear copolymers of the present invention are formed from monomers which form a homopolymer having a specified glass transition temperature, or $T_g$, as specified herein. The linear copolymers are also described by a preferred $T_g$. $T_g$ is a well known term of art in polymer science used to describe the temperature at which a polymer or portion thereof undergoes a transition from a solid or brittle material to a liquid or rubber-like material. Glass transition temperatures can be measured using standard techniques that are well known to the polymer scientist of ordinary skill in the art. One particularly useful technique for determining glass transitions is differential scanning calorimetry (also known as DSC). The glass transition phenomenon in polymers is described in *Introduction to Polymer Science and Technology: An SPE Textbook*, (eds. H. S. Kaufman and J. J. Falcetta), (John Wiley & Sons: 1977).

The linear copolymers hereof, when dried to form a film have a Tg of at least about 30° C., so that they are not unduly sticky, or "tacky" to the touch. Linear copolymers having this Tg tend to have low stickiness and provide good style hold. Preferred linear copolymers have a Tg of from about 35° to about 75° C., most preferably from about 35° to about 60° C. Such polymers tend to provide good restyling benefits, e.g., where heated implements are used.

The copolymers of the present invention have a weight average molecular weight (in grams/mole) of at least about 10,000. There is no upper limit for molecular weight except that which limits applicability of the invention for practical reasons, such as viscosity, processing, aesthetic characteristics, formulation compatibility, etc. Generally the weight average molecular weight is less than about 5,000,000, more generally less than about 2,500,000, and typically less than about 1,500,000. Preferably, the weight average molecular weight is from about 10,000 to about 5,000,000, more preferably from about 75,000 to about 2,500,000, even more preferably from about 100,000 to about 1,500,000, and most preferably from about 125,000 to about 1,000,000. Weight average molecular weight, for purposes hereof, can be measured by methods known in the art suitable for determining molecular weight of the sample to be analyzed, for example size exclusion chromatography utilizing column pore sizes of $10^3$, $10^5$ and $10^6$ angstroms, or other equivalent method.

The hair styling polymers consist essentially of monomer units which am hydrophobic monomers. The linear copolymers of the present invention are formed from the random copolymerization of (a) one or more hydrophobic monomer units that would form a homopolymer having a Tg of at least about 90° C., preferably at least about 100° C., more preferably at least about 110° C. (referred to herein as "A monomer units" or "A monomers") and (b) one or more hydrophobic monomers that would form a homopolymer having a Tg of less than about 25° C. (referred to herein as "B monomer units" or "B monomers").

The A and B monomers are selected from copolymerizable monomers, preferably ethylenically unsaturated monomers. By "copolymerizable", as used herein, is meant monomers that can be copolymerized using any conventional synthetic techniques. Monomers that are copolymerizable using conventional free radical initiated techniques are preferred. The term "ethylenically unsaturated" is used herein to mean monomers that contain at least one polymerizable carbon-carbon double bond (which can be mono-, di-, tri-, or tetra-substituted). The copolymer preferably consists essentially of monomers that when copolymerized, form a saturated polymer.

The linear copolymers comprise from about 5% to about 90%; preferably from about 10% to about 70%; most preferably from about 10% to about 50% of A monomers; and from about 10% to about 95%; preferably from about 30% to about 90%; most preferably from about 50% to about 90% of B monomers. These combinations of monomers provide the unique and useful properties of these materials, including non-tack, high Tg, good adhesive properties, and solubility.

The A and B monomers can be selected from a wide variety of structures as long as the limitations of the copolymer are met (i.e., solubility, $T_g$'s, and molecular weights described herein).

Preferred A monomers are indene, norbornylene, β-pinene, α-pinene, tert-butyl styrene, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, isobornyl acrylate, isobornyl methacrylate and combinations thereof. More preferred A monomers are indene, norbornene, norbornylene, tert-butyl styrene, isobornyl methacrylate and combinations thereof.

Preferred B monomers include $C_1$–$C_{18}$ alkyl esters of (meth)acrylic acid, preferably selected from the following alkyl esters of acrylic acid: n-butyl, dodecyl, 2-ethylhexyl, cyclohexyl, 2-ethylbutyl, n-ethyl, n-heptyl, n-hexyl, iso-butyl, iso-decyl, iso-propyl, 3-methylbutyl, 2-methylpentyl, nonyl, octyl, propyl; the following alkyl esters of methacrylic acid: n-butyl, dodecyl, 2-ethylhexyl, hexyl, decyl, 1-hexadecyl, hexyl, octadecyl, octyl, n-pentyl, tridecyl; vinyl esters, e.g., vinyl neodecanoate; and combinations thereof. More preferred B monomers include n-butyl acrylate, 2-ethylhexyl acrylate, 3-methylbutyl acrylate, 2-ethylbutyl acrylate, iso-propyl acrylate, n-butyl methacrylate, 2-ethylhexyl methacrylate, hexyl methacrylate, n-pentyl methacrylate, cyclohexyl acrylate, hexadecyl methacrylate, and combinations thereof. More preferably, the B monomers are selected from iso-propyl acrylate, cyclohexyl acrylate, 2-ethylhexyl methacrylate, hexyl methacrylate, hexadecyl methacrylate, n-butyl methacrylate, n-pentyl methacrylate and combinations thereof.

By appropriate selection and combination of the particular A and B monomers, and by the choice of specific relative ratios of the monomers well within the ability of one of ordinary skill in the art in light of the teachings herein, the copolymers can be optimized for various physical properties such as water and solvent solubility, $T_g$'s, and the like, and for compatibility with other ingredients commonly used in hair care applications.

PREFERRED POLYMERS OF THE PRESENT INVENTION

Particularly preferred random linear copolymers for use in the present invention include the following (the weight percents below refer to the amount of reactants added in the polymerization reaction, not necessarily the amount in the finished polymer):

Poly[indene-co-2-ethylhexyl methacrylate] (35:65 wt/wt)
Poly[tert-butyl styrene-co-n-ethyl acrylate] (50:50 wt/wt)
Poly[tert-butyl styrene-co-cyclohexyl acrylate] (70:30 wt/wt)
Poly[isobornyl acrylate-co-2-ethylhexyl acrylate] (70:30 wt/wt)
Poly[isobornyl methacrylate-co-vinyl 2-ethylhexanoate] (70:30 wt/wt)

Synthesis of the Linear Copolymers

The linear copolymers comprising randomly repeating A monomer units and B monomer units can be made by free radical polymerization of the A monomers with the B monomers. It is not intended to necessarily exclude from this invention any copolymers made by means other than free radical polymerization, so long as the product has the desired properties of $T_g$, solubility and molecular weight. The general principles of free radical polymerization methods are well understood. See, for example, Odian, "Principles of Polymerization", 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 10% to about 50%, on a weight basis. Undesired terminators, especially oxygen, can be removed as needed. This is done by evacuation or by purging with an inert gas, such as argon or nitrogen. The initiator is introduced and the reaction brought to the temperature needed for initiation to occur, assuming thermal initiators are used. Nonlimiting examples of suitable initiators include those selected from the group consisting of azo initiators, peroxide initiators, redox initiators, and photochemical initiators. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as needed utilizing a variety of techniques including filtration, extraction, membrane separation, gel permeation chromatography, and like.

There are numerous variations on these procedures which are entirely up to the discretion of the synthetic chemist (e.g., choice of degassing method and gas, choice of initiator type, extent of conversion, reaction loading, etc). The choice of initiator and solvent are often determined by the requirements of the particular monomers used, because different monomers have different solubilities and different reactivities to a specific initiator.

Analysis of the copolymer reaction product and the extracted materials, and the purified copolymer can be performed by conventional analysis techniques known in the art. These include, for example, nuclear magnetic resource (NMR), infrared molecular spectroscopies, gel permeation/size exclusion chromatography, membrane osmometry, and atomic absorption and emission spectroscopies.

Solvent For The Linear Copolymer

The compositions of the present invention comprise a hydrophobic, volatile, branched chain hydrocarbon liquid which is a solvent for the copolymers of the present invention. In general, the present compositions will comprise from about 0.1% to about 50%, preferably from about 0.2% to about 25%, and more preferably from about 0.5% to about 15%, of the solvent. The weight ratio of linear copolymer to solvent is generally from about 1:100 to about 5:1, preferably from about 1:10 to about 1:1, more preferably from about 1:8 to about 2:3.

As used herein, the term "volatile" refers to liquids having a boiling point at one atmosphere of 260° C. or less, preferably 250° C. or less, more preferably 230° C. or less, most preferably 225° C. or less. In addition, the boiling point of the volatile solvents will generally be at least about 50° C., preferably at least about 100° C. The term "nonvolatile", on the other hand, shall refer to materials which have a boiling point at one atmosphere of greater than 260° C. The hydrocarbon solvent should also be acceptable for topical application to the hair and skin (i.e., no undue irritation, sensitization or other reactions are induced by the solvent).

Preferred branched chain hydrocarbons contain from about 10 to about 16, more preferably from about 12 to about 16, most preferably from about 12 to about 14 carbon atoms. (E.g., preferred branched chain hydrocarbons include $C_{10}$–$C_{16}$ branched chain hydrocarbons, $C_{11}$–$C_{14}$ branched chain hydrocarbons, and $C_{12}$ branched chain hydrocarbons). Saturated hydrocarbons are preferred, although it is not intended to exclude unsaturated hydrocarbons. Examples of such preferred branched chain hydrocarbons include isoparaffins of the above chain sizes. Isoparaffins are commercially available from Exxon Chemical Co.; examples include Isopar™ H and K ($C_{11}$–$C_{12}$ isoparaffins), and Isopar™ L ($C_{11}$–$C_{13}$ isoparaffins). Other suitable branched chain hydrocarbons are isododecane and isohexadecane. Isododecane is preferred and is commercially available from Preperse, Inc. (South Plainfield, N.J., U.S.A.) as Permethyl™ 99A.

The linear copolymer is soluble in the branched chain hydrocarbon solvent in the present compositions. In general, the copolymer should be soluble at 25° C. at a concentration of 0.1% by weight of the hydrocarbon solvent, preferably at 1%, more preferably at 5%, most preferably at 15%.

The hydrocarbon solvent, however, is insoluble in aqueous carriers of the composition. This is determined in the absence of the copolymer, or other emulsifying agents, and can easily be verified by observing whether the solvent and aqueous carrier form separate phases after being mixed together at room temperature (as viewed without magnification).

Without intending to be necessarily limited by any particular theory, it is believed that preferred hydrocarbon solvents, having a boiling point of greater than about 100° C. (and more preferably less than about 200° C.), aid in obtaining a smoother polymer film upon drying. Since such hydrocarbon solvents are less volatile than the aqueous polymer phase, the hydrocarbon solvent maintains the copolymer in solubilized form for a relatively long period as the composition dries, thus minimizing aggregation of the copolymer, therefore, allowing the copolymer to dry as a smoother film. The compositions of the present invention may optionally include other volatile diluents or solvents. Such other diluents/solvents may include hydrocarbons, esters, ethers, alkyl alcohols, silicon derivatives, and mixtures thereof. However, preferred compositions do not include such other solvents.

Hair Care Compositions

The compositions of the present invention also comprise a suitable carrier or hair care matrix for delivering the copolymer and the hydrophobic, volatile, branched hydrocarbon solvent to the hair. Any carrier suitable for delivery of the copolymer/hydrocarbon solvent to the hair can be used. The carrier can comprise a volatile liquid which is water or is otherwise water soluble, or a mixture thereof and in which the volatile solvent of the copolymer is not soluble. In general, the compositions will comprise from about 50% to about 99.3%, preferably from about 70% to about 99%, more preferably from about 85% to about 98%, of carrier or hair care matrix.

The carrier liquid herein can include water and other hydrophilic fluids, and combinations thereof. Suitable carrier fluids for use in the present invention, in addition to water, include lower alcohols ($C_1$–$C_4$ alcohols, preferably $C_2$–$C_4$ alcohols such as ethanol and isopropanol) and mixtures of lower alcohols. Preferred solvents include water, ethanol, and mixtures thereof. Especially preferred is water.

The preferred compositions are in the form of a discontinuous phase of dispersed droplets, or particles, of the copolymer and the hydrophobic, volatile solvent distributed throughout the carrier. The carrier can also comprise a variety of other components, such as other active ingredients, rheology modifiers such as thickeners, gelling agents, etc. The compositions of the present invention can be in the form of liquids, lotions, creams gels, etc.

The carrier may include gel vehicle materials or other rheology modifiers. These are particularly contemplated for use in products such as hair rinses, shampoos, mousses, and creams and lotions.

Gel vehicles can comprise two essential components: a lipid vehicle material and a surfactant vehicle material. Gel vehicles are generally described in the following documents: Barry, "The Self Bodying Action of the Mixed Emulsifier Sodium Dodecyl Sulfate/Cetyl Alcohol", 28 J. of Colloid and Interface Science 82–91 (1968); Barry, et al., "The Self-Bodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000—Cetostearyl Alcohol, I. Self Bodying Action", 38 J. of Colloid and Interface Science 616–625 (1972).

The carrier may incorporate one or more lipid vehicle materials which are essentially water-insoluble, and which contain hydrophobic and hydrophilic moieties. Lipid vehicle materials include naturally or synthetically-derived acids, acid derivatives, alcohols, esters, ethers, ketones, and amides with carbon chains of frown about 12 to about 22, preferably from about 16 to about 18, carbon atoms in length. Fatty alcohols and fatty esters are preferred; fatty alcohols are particularly preferred.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Lipid vehicle materials among those useful herein are disclosed in *Bailey's Industrial Oil and Fat Products*, (3rd edition, D. Swern, ed., 1979). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin; et al., issued May 26, 1981; British Specification 1,532,585, published Nov. 15, 1978; and Fuku Shima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976. If included in the compositions of the present invention, the lipid vehicle material is typically present at from about 0.1% to about 10.0% of the composition; the cationic surfactant vehicle material is present at from about 0.05% to about 5.0% of the composition.

Cationic surfactant materials are suitable for use in the gel vehicles and include, but are not limited to, those described in detail below. The compositions hereof can also contain a lipid vehicle without the inclusion of a cationic surfactant.

The use of nonionic cellulose ethers and water-soluble gums for thickening compositions is also contemplated. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum.

Nonionic water-soluble cellulose ethers are preferred polymers that can be employed in hair care compositions. Cellulose ethers are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.). Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Other carrier ingredients for use ill the compositions of the present invention, especially for hair rinses, include combinations of one or more nonionic, water soluble polymeric materials that have been hydrophobically-modified (hereinafter alternatively referred to as "hydrophobically modified nonionic water-soluble polymer"), with one or more surfactants, such as quaternary ammonium compounds (such as ditallowdimethyl ammonium chloride). These vehicles are described in detail in the following patents: U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al, and U.S. Pat. No. 5,100,657, issued Mar. 31, 1992 to Ansher-Jackson et al.

These systems provide a gel-like rheology without necessarily being gels in the technical sense. When such systems are used to thicken the present compositions, from about 0.3% to about 5.0%, preferably from about 0.4% to about 3.0%, of the hydrophobically modified nonionic water-soluble polymer is preferably utilized with from about 0.3% to about 5.0%, preferably from about 0.4% to about 3.0%, of a water-soluble polymeric thickening material such as described herein.

By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C.

The polymer backbone of the hydrophobically modified nonionic water-soluble polymer can be essentially any water-soluble polymer. Examples of water soluble polymers useful for forming the hydrophobically modified nonionic water-soluble polymer include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone, dextrans, for example Dextran purified crude Grade 2P, available from D&O Chemicals, plant exudates such as acacia, ghatti, and tragacanth, seaweed extracts such as sodium alginate, propylene glycol alginate, sodium carrageenan, cationic polymers such as Ucare JR-polymer (a cationic modified hydroxyethyl cellulose available from Union Carbide), natural polysaccharide materials, such as guar gum, locust bean gum, and xanthan gum. Nonionic water-soluble cellulose ethers are preferred to be employed as the polymer substrate of such hydrophobically modified polymers. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The hydrophobic groups which modify the nonionic water-soluble polymer can be $C_8$ to $C_{22}$ alkyl, aryl alkyl, alkyl aryl groups and mixtures thereof. One or more hydrophobic groups can be attached to the cellulose ether substrate via an ether, ester or urethane linkage. The ether linkage is preferred.

The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1. One commercially available hydrophobically modified nonionic water-soluble polymer material which meets the foregoing requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

The hydrophobically modified nonionic water-soluble polymer can be used in combination with water soluble or water insoluble surfactants.

In this regard, "water-soluble surfactant" means surfactant materials which form substantially clear, isotropic solutions when dissolved in water at 0.2 weight percent at 25° C. The water-soluble surfactant preferably has a molecular weight of less than about 20,000.

Essentially any water-soluble surfactant material which meets these requirements will work in the present invention. However, the following materials have been found to be particularly preferred: cetyl betaine, ammonium lauryl sulfate, ammonium laureth sulfate; cetyl trimethyl ammonium chloride, and mixtures thereof.

When such systems are used to thicken the present compositions, from about 0.1% to about 10.0%, preferably from about 0.2% to about 5.0%, of the hydrophobically-modified nonionic water soluble polymer is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

By "water-insoluble surfactant" for use in such systems it is meant surfactant materials which do not form substantially clear isotropic solutions when dissolved in water at greater than 0.2 weight percent at 25° C. The water-insoluble surfactant preferably has a molecular weight of less than about 20,000. Essentially any water-insoluble surfactant material which meets these requirements will work in the present invention, however, water-insoluble cationic surfactant materials are preferred. Cationic surfactants are described below. The following nonexclusive materials are suitable: stearamide diethanolamine (stearamide DEA), cocoamide methanolamine (cocoamide MEA), dimethyl stearamine oxide, glyceryl monooleate, sucrose stearate, PEG-2 stearamine, polyethylene glycol ethers of fatty alcohols, such as Cetheth-2 of the formula $CH_3\text{---}(CH_2)_{14}\text{---}CH_2\text{---}(OCH_2CH_2)_n\text{---}OH$, where n has an average value of 2 (commercially available under the trade name Brij 56 from ICI Americas), glycerol stearate citrate, dihydrogenated tallow dimethyl ammonium chloride, polyoxyethylene, polyoxypropylene block polymers such as Poloxamer 181, of the formula:

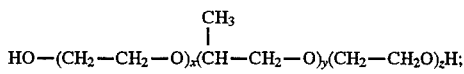

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified nonionic polymer is generally utilized with from about 0.02% to about 10.0%, preferably from about 0.05% to about 3.0%, most preferably from about 0.05% to about 2.0%, of the water-insoluble surfactant.

Cationic surfactants useful in the compositions of the present invention, including the gel vehicle systems as well as hydrophobically modified nonionic polymer systems, include those containing amino or quaternary ammonium hydrophilic moieties which are positively charged when dissolved in the aqueous composition of the present invention. Cationic surfactants among those useful herein are disclosed in more detail below.

It is also contemplated to utilize a suspending agent to thicken the compositions and/or to suspend the copolymer branched hydrocarbon solvent phase in the carrier. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfiled, Ill. U.S.A.).

Surfactants

Surfactants are optional ingredients in the compositions of the invention, particularly shampoo and conditioner compositions. When present, the surfactant typically comprises from about 0.05% to about 50% of the composition. For a shampoo, the level is preferably from about 10% to about 30%, most preferably from about 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for shampoo compositions, include alkyl and alkyl ether sulfates. These materials typically have the respective formulae $ROSO_3M$ and $RO(C_2H_4O)xSO_3M$, wherein R is alkyl or alkenyl of from about 10 to about 20 carbon atoms, x is 1 to 10, and M is a water-soluble cation such as ammonium, sodium, potassium and triethanolamine.

Another suitable class of anionic surfactants are the water-soluble salts of the organic, sulfuric acid reaction products of the general formula:

$$R_1\text{---}SO_3\text{---}M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12\text{-}18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuc cinicacid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The α-olefins from which the olefin sulfonates are derived are mono-olefins having about 12 to about 24 carbon atoms, preferably about 14 to about 16 carbon atoms. Another class of anionic organic surfactants are the β-alkyloxy alkane sulfonates. These compounds have the following formula:

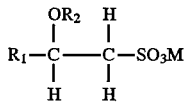

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers*, 1984 Annual, published by Allured Publishing Corporation. Also U.S. Pat. No. 3,929,678, Laughlin et al., issued Dec. 30, 1975, discloses many other anionic as well as other surfactant types.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. Those derived from the condensation of ethylene oxide with the product resulting from the reaction of propylene oxide and ethylene diamine products.

2. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

3. Long chain tertiary amine oxides such as those corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals (the arrow in the formula is a conventional representation of a semipolar bond).

4. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

5. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetra decyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, include those containing amino or quaternary ammonium hydrophilic moieties which are positively charged when dissolved in the aqueous composition of the present invention. Cationic surfactants among those useful herein are disclosed in the following documents: M.C. Publishing Co., McCutcheon's, Detergents & Emulsifier, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

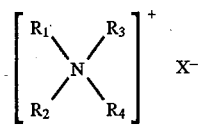

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethylammonium chlorides, wherein the alkyl groups have from about 12 to about 22 carbon atoms and am derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieocosyol dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(saturated or unsaturated tallow) dimethyl ammonium chloride is a particularly preferred quaternary ammonium salt.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981.

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

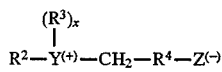

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds filling within this definition are sodium 3-dodecyl-aminopropionate, sodium 3-dodecylamino propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Silicone Hair Conditioning Agent

An optional component of the present invention is a nonvolatile, silicone conditioning agent which is not soluble in the aqueous or water soluble phase of compositions wherein the carrier is aqueous-based or otherwise based on water soluble solvents.

The silicone hair conditioning agent for use herein will preferably have an average viscosity of from about 1,000 to about 20,000,000 centistokes at 25° C., more preferably from about 10,000 to about 10,000,000, even more preferably from about 100,000 to about 5,000,000. The viscosity of silicones herein can, in general, be measured by means of a glass capillary viscometer as set forth in Dow Corning Corporate Test Method CTM0004, Jul. 20, 1970.

The silicone hair conditioning agent will typically be used in the shampoo compositions hereof at levels of from about 0.05% to about 10% by weight of the composition, preferably from about 0.1% to about 10%, more preferably from about 0.5% to about 8%, most preferably from about 0.5% to about 5%.

Suitable nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

Silicone fluids hereof also include polyalkyl or polyaryl siloxanes with the following structure:

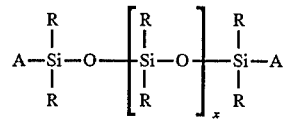

wherein R is alkyl or aryl, and x is an integer from about 1 to about 8,000 may be used, preferably from about 5 to about 8,000. "A" represents groups which block the ends of the silicone chains.

The alkyl or aryl groups substituted on the siloxane chain (R) or at the ends of the siloxane chains (A) may have any structure as long as the resulting silicones are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy propoxy and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil® and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Cationic Polymer Hair Conditioning Agent

The compositions of the present invention can also comprise a water soluble, cationic organic polymer conditioning agent for hair. The polymeric cationic conditioning agent hereof will generally be present at levels of from about 0.05% to about 5%, preferably from about 0.1% to about 4%, more preferably from about 0.2% to about 3%, by weight, of the shampoo composition. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The cationic organic polymers useful in the hair conditioning agent hereof are organic polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

The cationic charge density is preferably at least about 0.9 meq/gram, more preferably at least about 1.0 meq/gram, even more preferably at least abut 1.1 meq/gram, most preferably at least about 1.2 meq/gram. The cationic charge density is preferably no greater than about 4 meq/gram, more preferably no greater than about 3.0 meq/gram, most preferably no greater than about 2.0 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use, which will in general be from about pH 3 to about pH 9, most generally from about pH 4 to about pH 8.

Any anionic counterions can be utilized for the cationic polymers so long as the water solubility criteria is met. Suitable counterions include halides (e.g., Cl—, Br—, I—, or F—, preferably Cl—, Br—, or I—), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT tradename (e.g., LUVIQUAT FC 370); copolymers of 1-vinyl-2- pyrrolidone and dimethylaminoethyl methacrylate (referred to in the industry by CTFA as Polyquaternium-11) such as those commercially available from ISP Corporation (Wayne, N.J., U.S.A.); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquatemium 7, respectively; and mineral acid salts of amino-alkyl esters of homo- and co-polymers of unsaturated carboxylic acids having from 3 to 5 carbon atoms, as described in U.S. Pat. No. 4,009,256.

Other cationic polymers that can be used include polysaccharide polymers, such as cationic cellulose derivatives and cationic starch derivatives.

Cationic polysaccharide polymer materials suitable for use herein include those of the formula:

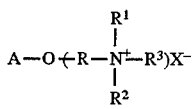

wherein:

A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., U.S.A.) in their Polymer JR$^R$ and LR$^R$ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., U.S.A.) under the tradename Polymer LM-200.

Other cationic polymers that can be used include cationic guar gum derivatives, such as guar hydroxypropyltrimonium chloride (commercially available from Celanese Corp. in their Jaguar® series). Other materials include quaternary nitrogen-containing cellulose ethers (e.g., as described in U.S. Pat. No. 3,962,418), and copolymers of etherified cellulose and starch (e.g., as described in U.S. Pat. No. 3,958,581).

Organic Oil Conditioning Agents

The compositions of the present invention can also comprise a nonvolatile, water insoluble, organic, oil as a conditioning agent for hair. The hair conditioning oily liquid can add shine and luster to the hair. The conditioning oil is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The conditioning oil hereof generally will have a viscosity of about 3 million cs or less, preferably about 2 million cs or less, more preferably about 1.5 million cs or less.

The conditioning oils hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain more than 16 carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be at least about 400, preferably at least about 500, more preferably at least about 600. Specific examples of suitable materials include paraffin oil, mineral oil, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of eicosane, such as 2,2,4,4,6,6,8,8-10-nonylmethylundecane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill. U.S.A.).

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyol stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and all-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

The compositions herein can contain a variety of other optional components suitable for rendering such compositions more cosmetically or aesthetically acceptable or to provide them with additional usage benefits, e.g. medicinal benefits. Such conventional optional ingredients are well-known to those skilled in the art, e.g., sunscreens, medicaments (e.g. anti-bacterials, anti-inflamatories, anti-acne actives, etc.), colors and dyes, perfumes, pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, diisobutyl adipate, butyl stearate, and propylene glycol. Such optional ingredients generally are used individually at levels of from about 0.01% to about 10.0%, preferably from about 0.05% to about 5.0%, of the composition.

The pH of the present compositions generally will be between about 3 and about 9, preferably between about 4 and about 8.

As with all compositions, the present invention should not contain components which unduly interfere with the performance of the compositions.

The hair care compositions of the present invention can be made using conventional formulation and mixing techniques. Methods of making various types of cosmetic compositions are described more specifically in the following examples.

Method of Using Hair Care Compositions

The hair care compositions of the present invention are used in conventional ways to provide the desired benefit appropriate to the product such as hair styling, holding, cleansing, conditioning and the like for hair care compositions. Such methods of use depend upon the type of composition employed but generally involve application of an effective amount of the product to the hair, which may then be rinsed from the hair (as in the case of shampoos and some conditioning products) or allowed to remain on the hair (as in the case of spray, mousse, or gel products). The present invention is especially adapted for rinse off hair care compositions. By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example 1

Synthesis of poly[indene-co-2-ethylhexyl methacrylate] (35:65 wt/wt):

Add 0.5 grams azobisisobutryonitrile (AIBN) initiator to a solution of 35.0 grams of indene and 65 grams of 2-ethylhexyl methacrylate in 500 mL of tetrahydrofuran (THF). Reflux the resulting solution slowly for about 20 hours, then quench the reaction by adding about 5 mL of methanol. Pour the solution into a pan and evaporate the THF at room temperature. Redissolve the resulting polymer film in THF and then precipitate the polymer in methanol. Dry the resulting polymer.

Example 2

Prepare the following copolymers using the method described in Example 1 by varying the reaction components as noted:

a) Poly[tert-butyl styrene-co-n-ethyl acrylate] (50:50 wt/wt)
b) Poly[isobornyl acrylate-co-2-ethylhexyl acrylate] (70:30 wt/wt)
c) Poly[tert-butyl styrene-co-cyclohexyl acrylate] (70:30 wt/wt)
d) Poly[isobornyl methacrylate-co-vinyl 2-ethylhexanoate] (70:30 wt/wt)

Examples 3–5

The following hair styling/conditioning rinse compositions are representative of the present invention.

| Composition Conditioner Premix | 3 wt. % | 4 wt. % | 5 wt. % |
|---|---|---|---|
| Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Copolymer in Example 1 | 1.75 | 1.75 | 1.75 |
| Permethyl 99A | 8.54 | 8.54 | 8.54 |
| Trimethysiloxysilicate | 0.11 | 0.11 | 0.00 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Decamethyl cyclopentasiloxane/ Polydimethyl Siloxane Gum solution[3] | 1.67 | 1.67 | 2.33 |
| Adogen 470[4] | 0.70 | 0.60 | 0.93 |
| Adogen 471[5] | 0.05 | 0.15 | 0.07 |
| trimethylsilyl amodimethicone[6] | 0.10 | 0.10 | 0.10 |
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellullose from Aqualon Corp.
[2]Readily dispersible xantham gum
[3]SE-76 gum available From General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.
[6]Dow Corning Q2-8220

Prepare the styling polymer premix by combining the polymer, permethyl 99A, and silicone resin.

Prepare the silicone premix by combining and mixing (in a separate vessel) water, Adogen 470 and Adogen 471 at 85° C. Cool to 71° C. and add the silicone gum/decamethyl cyclopentasiloxane solution and trimethylsilylamodimethicone and mix until homogeneous. Cool to 38° C. while using a homogenizer (such as Tekmar).

Prepare the surfactant premix by combining and mixing (in a separate vessel) the water and Stearalkonium Chloride at 38° C.

Prepare the conditioner premix by combining and mixing (in a separate vessel) to the DRO water heated to 71° C.: citric acid, sodium citrate, cetyl alcohol, stearyl alcohol and Natrosol Plus CS grade D-67 and mixing until homogeneous. Add the xanthan gum and mix until homogeneous. Add the styling polymer premix, Kathon CG and perfume and mix until homogeneous. Further disperse the composition with an in-line homogenizer (such as Tekmar homogenizer) and then cool to 38° C.

Complete the conditioner by combining and mixing (in a separate vessel) the conditioner premix, the silicone premix and the surfactant premix at 38° C., then cool this mixture to 25° C.

Apply the compositions defined in Examples 3–5 to the hair in the conventional manner to provide effective hair conditioning and styling/hold benefits without leaving the hair with a sticky/stiff feel.

Example 6

Polymer Premix with added Drying Aid

Prepare the following premix utilizing conventional mixing techniques.

| Ingredients | Weight % |
|---|---|
| Copolymer in Example 2(a) | 16.83 |
| Permethyl 99A | 83.17 |
| Trimethylsiloxysilicate | 1.00 |

Prepare this mix by adding the copolymer to the solvents while mixing. Heat to 80°–84° C. in a covered vessel, maintaining mixing. Cool to 23°–27° C. and add trimethylsiloxysilicate while mixing.

Example 7

Polymer Premix with added Drying Aid

Prepare the following premix utilizing conventional mixing techniques.

| Ingredients | Weight % |
|---|---|
| Copolymer in Example 2(a) | 15.00 |
| Isododecane | 83.50 |
| Polydimethylsiloxane (Dow Corning 200 Fluid (20 csk)) | 1.50 |

Prepare this mix by adding the copolymer to the solvent while mixing. Heat to 80°–84° C. in a covered vessel, maintaining mixing. Cool to 23°–27° C. and add polydimethylsiloxane while mixing.

Example 8

Hair Conditioner

Prepare a hair conditioner composition from the following components utilizing conventional mixing techniques.

| Ingredient | Weight % A | Weight % B |
|---|---|---|
| Styling Agent Premix | | |
| Styling Polymer Premix of Example 3[1] | 10.00 | 10.00 |
| Silicone Premix | | |
| Silicone gum, GE SE76[2] | 0.30 | 0.30 |
| Octamethyl cyclotetrasiloxane | 1.70 | 1.70 |
| Main Mix | | |
| Water | QS100 | QS100 |
| Cetyl Alcohol | 1.00 | — |
| Quaternium 18[3] | 0.85 | 0.85 |
| Stearyl Alcohol | 0.70 | — |
| Hydroxyethyl Cellulose | 0.50 | — |
| Cetyl Hydroxyethyl Cellulose[4] | — | 1.25 |
| Ceteareth-20 | 0.3 | — |
| Fragrance | 0.20 | 0.20 |
| Dimethicone copolyol | 0.20 | — |
| Citric Acid | 0.13 | 0.13 |
| Methylchloroisothiazolinone (and) methylisothiazolinone | 0.04 | 0.04 |
| Sodium Chloride | 0.01 | 0.01 |
| Xanthan Gum | — | 0.20 |

[1]Alternatively, conditioner compositions are prepared with polymer premix from Example 7.
[2]Commercially available from General Electric.
[3]Dimethyl Di(Hydrogenated Tallow) Ammonium Chloride
[4]Commercially available as Polysurf D-67 from Aqualon.

Prepare the product by comixing all the Main Mix ingredients, heating to about 60° C. with mixing. Cool the mixture to about 45° C. with colloid milling (Example A) or mixing (Example B). At this temperature, add the two premixes separately with moderate agitation. Cool the resulting conditioner to room temperature.

Example 9

Shampoo Composition

Prepare a shampoo composition from the following components utilizing conventional mixing techniques.

| Ingredients | Weight % |
| --- | --- |
| Styling Agent | |
| Styling Polymer Premix from Example 3 Premix | 15.00 |
| Silicone gum | 0.50 |
| Dimethicone, 350 cs fluid | 0.50 |
| Main Mix | |
| Water | QS100 |
| Ammonium lauryl sulfate | 11.00 |
| Cocamide MEA | 2.00 |
| Ethylene glycol distearate | 1.00 |
| Xanthan Gum | 1.20 |
| Methylchloroisothiazolinone (and) methylisothiazolinone | 0.04 |
| Citric Acid to pH 4.5 as needed | |

Prepare the Main Mix by first dissolving the xanthan gum in the water with conventional mixing. Add the remaining Main Mix ingredients and heat to 150° F. with agitation for ½ hour. Add the Styling Agent and the Premix sequentially with about 10 minutes of agitation between additions, and stir the entire mixture while the batch is cooled to room temperature. For varied particle size, add the Styling Agent and Premix at different times using either or both high shear mixing (high speed dispersator) or normal agitation.

Apply the shampoo to the hair for cleansing the hair and for providing a styling benefit.

While particular embodiments of the subject invention have been described, it will be obvious to those skilled in the an that various changes and modifications to the subject invention can be made without departing from the spirit and scope of the invention. It is intended to cover, in the appended claims, all such modifications that are within the scope of the subject invention.

What is claimed is:

1. A hair care composition comprising:
    a) a hydrophobic linear random copolymer formed from the copolymerization of A monomer units and B monomer units, said A monomer units being copolymerizable with said B monomer units and selected from monomer units that form a homopolymer having a $T_g$ of at least about 90° C., said B monomer units being copolymerizable with said A monomer units and selected from monomer units that form a homopolymer having a $T_g$ of less than about 25° C.; wherein said copolymer comprises:
        (i) from about 5% to about 90% by weight of said A monomer units, and
        (ii) from about 95% to about 10% by weight of said B monomer units;
    said copolymer comprising randomly repeating units of said A monomer units copolymerized with said B monomer units, said copolymer having a weight average molecular weight greater than about 10,000 and a Tg of at least about 30° C.; and
    b) a hydrophobic, volatile, hydrocarbon solvent for said copolymer, said solvent consisting essentially of one or more branched chain hydrocarbons containing from 10 to 16 carbon atoms;
    wherein the weight ratio of said copolymer to said solvent is from about 1:100 to about 5:1.

2. The composition of claim 1 wherein said A monomer units are selected from monomer units that form a homopolymer having a $T_g$ of at least about 100° C.

3. The composition of claim 2 wherein said A monomer units are selected from monomer units that form a homopolymer having a $T_g$ of at least about 110° C.

4. The composition of claim 1 wherein said A monomer units are selected from the group consisting of indene, norbornylene, β-pinene, tert-butyl styrene, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, isobornyl acrylate, isobornyl methacrylate, and combinations thereof.

5. The composition of claim 4 wherein said A monomer units are selected from the group consisting of indene, norbornene, norbornylene, tert-butyl styrene, isobornyl acrylate, isobornyl methacrylate, and combinations thereof.

6. The composition of claim 1 wherein said B monomer units are selected from $C_1$–$C_{18}$ alkyl esters of acrylic acid, $C_1$–$C_{18}$ alkyl esters of methacrylic acid, and combinations thereof.

7. The composition of claim 6 wherein said B monomer units are selected from the group consisting of the following alkyl esters of acrylic acid: n-butyl, dodecyl, 2-ethylhexyl, cyclohexyl, 2-ethylbutyl, n-ethyl, n-heptyl, n-hexyl, iso-butyl, iso-decyl, iso-propyl, 3-methylbutyl, 2-methylpentyl, nonyl, octyl, propyl; the following alkyl esters of methacrylic acid: n-butyl, dodecyl, 2-ethylhexyl, hexyl, decyl, 1-hexadecyl, hexyl, octadecyl, octyl, n-pentyl, tridecyl; and combinations thereof.

8. The composition of claim 7 wherein said B monomer units are selected from the group consisting of n-butyl acrylate, 2-ethylhexyl acrylate, 3-methylbutyl acrylate, 2-ethylbutyl acrylate, iso-propyl acrylate, n-butyl methacrylate, 2-ethylhexyl methacrylate, hexyl methacrylate, n-pentyl methacrylate, cyclohexyl acrylate, hexadecyl methacrylate, and combinations thereof.

9. The composition of claim 8 wherein said B monomer units are selected from the group consisting of iso-propyl acrylate, cyclohexyl acrylate, 2-ethylhexyl methacrylate, hexyl methacrylate, hexadecyl methacrylate, n-butyl methacrylate, n-pentyl methacrylate and combinations thereof.

10. The composition of claim 1 wherein said copolymer comprises from about 10% to about 70% of said A monomer units and from about 30% to about 90% of said B monomer units.

11. The composition of claim 10 wherein said copolymer comprises from about 10% to about 50% of said A monomer units and from about 50% to about 90% of said B monomer units.

12. The composition of claim 1 wherein said copolymer has a $T_g$ of from about 35° C. to about 60° C.

13. The composition of claim 1 wherein said hydrophobic, volatile, branched hydrocarbon solvent is selected from the group consisting of branched chain hydrocarbons containing from 12 to 16 carbon atoms and combinations thereof.

14. The composition of claim 13 wherein said hydrophobic, volatile, hydrocarbon solvent is selected from the group consisting of branched chain hydrocarbons containing from 12 to 14 carbon atoms and combinations thereof.

15. The composition of claim 14 wherein said hydrophobic, volatile, hydrocarbon solvent comprises isododecane.

16. The composition of claim 1 wherein the weight ratio of said copolymer to said solvent is from about 1:8 to about 2:3.

17. The composition of claim 1 comprising from about 0.1% to about 25%, by weight, of said copolymer and from about 0.1 to about 50%, by weight, of said solvent.

18. The composition of claim 1 further comprising a carrier for said copolymer and said solvent, said carrier comprising water or a hydrophilic fluid.

19. A hair care composition comprising:
a) a hydrophobic linear random copolymer formed frown the copolymerization of A monomer units and B monomer units, said A monomer units being copolymerizable with said B monomer units and selected from the group consisting of indene, norbornylene, β-pinene, tert-butyl styrene, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, isobornyl acrylate, isobornyl methacrylate, and combinations thereof;

said B monomer units being copolymerizable with said A monomer units and selected from $C_1$–$C_{18}$ alkyl esters of acrylic acid, $C_1$–$C_{18}$ alkyl esters of methacrylic acid, and combinations thereof;

wherein said copolymer comprises:
   (i) from about 5% to about 90% by weight of said A monomer units, and
   (ii) from about 95% to about 10% by weight of said B monomer units; said copolymer comprising randomly repeating units of said A monomer units copolymerized with said B monomer units, said copolymer having a weight average molecular weight greater than about 10,000 and a Tg of at least about 30° C.; and (b) a hydrophobic, volatile, hydrocarbon solvent for said copolymer, said solvent consisting essentially of one or more branched chain hydrocarbons containing from 10 to 16 carbon atoms;

wherein the weight ratio of said copolymer to said solvent is from about 1:100 to about 5:1.

20. A method for styling hair comprising the step of applying the composition of claim 1 to the hair in an amount sufficient to style the hair.

21. A method for conditioning hair comprising the step of applying the composition of claim 1 to the hair in an amount sufficient to condition the hair.

* * * * *

UNITED STATES PATENT AND TRADEMARK OFFICE
CERTIFICATE OF CORRECTION

PATENT NO. : 5,662,892

DATED : September 2, 1997

INVENTOR(S) : Raymond E. Bolich, Jr. and Sanjeev Midha

It is certified that error appears in the above-identified patent and that said Letters Patent is hereby corrected as shown below:

At column 4, line 26 "which am" should read --which are--.

At column 8, line 11 "frown about" should read --from about--.

At column 8, line 29 "Villamarin; et al." should read --Villamarin, et al.--.

At column 9, line 7 "use ill the" should read --use in the--.

At column 10, line 40 "sulfate; cetyl" should read --sulfate, cetyl--.

At column 12, line 55 "issued. Dec." should read --issued Dec.--.

At column 13, line 55 "Emulsifier" should read --Emulsifiers--.

At column 14, line 22 "and am derived" should read --and are derived--.

At column 15, line 47 "compounds filling" should read --compounds falling--.

At column 16, lines 42-43 "ethoxy propoxy and" should read --ethoxy, propoxy, and--.

At column 19, line 9 "Polyquatemium 7" should read --Polyquaternium 7--.

At column 19, line 29 "alkoxalkyl" should read --alkoxyalkyl--.

At column 19, line 36 "Edison" should read --(Edison--.

At column 21, line 8 "all-fatty acid" should read --di-fatty acid--.

At column 21, line 32 "in the an" should read --in the art--.

At column 23, line 14 "Trimethysiloxysilicate" should read --Trimethylsiloxysilicate--.

At column 23, line 26 "cellullose" should read --cellulose--.

At column 25, line 3 insert "Apply the product to the hair as a rinse off hair conditioner."

UNITED STATES PATENT AND TRADEMARK OFFICE
CERTIFICATE OF CORRECTION

PATENT NO. : 5,662,892
DATED : September 2, 1997
INVENTOR(S) : Raymond E. Bolich, Jr. and Sanjeev Midha It is certified that error appears in the above-identified patent and that said Letters Patent is hereby corrected as shown below:

At column 25, line 40 "an that" should read --art that--.

At column 27, line 14 "frown the" should read --from the--.

Signed and Sealed this

Thirty-first Day of March, 1998

Attest:

BRUCE LEHMAN

*Attesting Officer*   Commissioner of Patents and Trademarks